(12) United States Patent
Burger et al.

(10) Patent No.: US 10,081,041 B2
(45) Date of Patent: Sep. 25, 2018

(54) FLATNESS MEASURING AND MEASURING OF RESIDUAL STRESSES FOR A METALLIC FLAT PRODUCT

(71) Applicant: PRIMETALS TECHNOLOGIES AUSTRIA GMBH, Linz (AT)

(72) Inventors: Rainer Burger, Nuremberg (DE); Ansgar Grüss, Erlangen (DE); Helmut Hlobil, Niederneukirchen (AT); Peter Hunt, Wimborne (GB); Robert Linsbod, Linz (AT)

(73) Assignee: PRIMETALS TECHNOLOGIES AUSTRIA GMBH (AT)

( * ) Notice: Subject to any disclaimer, the term of this patent is extended or adjusted under 35 U.S.C. 154(b) by 0 days.

(21) Appl. No.: 14/651,411

(22) PCT Filed: Nov. 25, 2013

(86) PCT No.: PCT/EP2013/074563
§ 371 (c)(1),
(2) Date: Jun. 11, 2015

(87) PCT Pub. No.: WO2014/090555
PCT Pub. Date: Jun. 19, 2014

(65) Prior Publication Data
US 2015/0354948 A1 Dec. 10, 2015

(30) Foreign Application Priority Data
Dec. 11, 2012 (AT) .............................. A 50572/2012

(51) Int. Cl.
*G01N 3/20* (2006.01)
*B21B 38/02* (2006.01)
(Continued)

(52) U.S. Cl.
CPC .............. *B21B 38/02* (2013.01); *B21C 51/00* (2013.01); *G01B 11/16* (2013.01); *G01B 11/24* (2013.01);
(Continued)

(58) Field of Classification Search
CPC ....... G01L 5/045; G01N 3/20; G01M 5/0041; G01B 11/306; G01B 11/24; B21B 38/02
(Continued)

(56) References Cited

U.S. PATENT DOCUMENTS 4,910,877 A * 3/1990 Sokol ...................... G01B 7/281
33/544
5,665,922 A * 9/1997 Tsukada ............ G01M 17/0078
73/849
(Continued)

FOREIGN PATENT DOCUMENTS

DE          197 25 726 A1    1/1999
DE    10 2007 059185 A1     7/2008
(Continued)

OTHER PUBLICATIONS

International Search Report dated Feb. 17, 2014 issued in corresponding International patent application No. PCT/EP2013/074563.

*Primary Examiner* — Max Noori
(74) *Attorney, Agent, or Firm* — Ostrolenk Faber LLP

(57) ABSTRACT

A method and apparatus for flatness measuring and measuring of residual stresses in a metallic flat product (1): The method includes bending the flat product (1) in a bending device (3) such that a planar flat product (1) forms an arc (5) with a target bending radius $r_0$ after bending; measuring the contour and the actual bending radii r(y), in the region of the arc (5) of the bent flat product (1) at a plurality of positions along the width direction of the flat product (1); and determining (Continued)

mining the flatness of the flat product (1) taking into account the measured contour of the bent flat product (1).

20 Claims, 6 Drawing Sheets

(51) Int. Cl.
    *G01B 11/24*     (2006.01)
    *B21C 51/00*     (2006.01)
    *G01B 11/30*     (2006.01)
    *G01B 21/20*     (2006.01)
    *G01B 11/16*     (2006.01)
    *B21B 3/00*     (2006.01)

(52) U.S. Cl.
    CPC ............ *G01B 11/306* (2013.01); *G01B 21/20* (2013.01); *G01N 3/20* (2013.01); *B21B 2003/001* (2013.01); *B21B 2261/06* (2013.01)

(58) Field of Classification Search
    USPC .................................. 73/849, 818, 862.637
    See application file for complete search history.

(56) References Cited

U.S. PATENT DOCUMENTS

| | | | | |
|---|---|---|---|---|
| 5,687,487 A * | 11/1997 | Johnson | ................. | G01B 7/345 33/501.02 |
| 6,255,664 B1 * | 7/2001 | Okawa | ................... | G01B 7/345 250/559.22 |
| 8,544,340 B1 * | 10/2013 | Ardelean | ................. | G01N 3/20 73/849 |
| 8,890,649 B2 * | 11/2014 | Saitou | ...................... | G01B 7/18 252/511 |
| 2008/0212065 A1 * | 9/2008 | Konetschny | ......... | G01C 15/002 356/3.01 |
| 2011/0228282 A1 * | 9/2011 | Yang | .................... | G01B 11/306 356/601 |
| 2012/0169869 A1 * | 7/2012 | You | ........................ | A63B 53/10 348/142 |
| 2014/0268175 A1 * | 9/2014 | Harn | .................... | G01B 11/306 356/601 |

FOREIGN PATENT DOCUMENTS

| | | |
|---|---|---|
| EP | 1 369 186 A2 | 12/2003 |
| JP | H 01 292208 | 11/1989 |

* cited by examiner

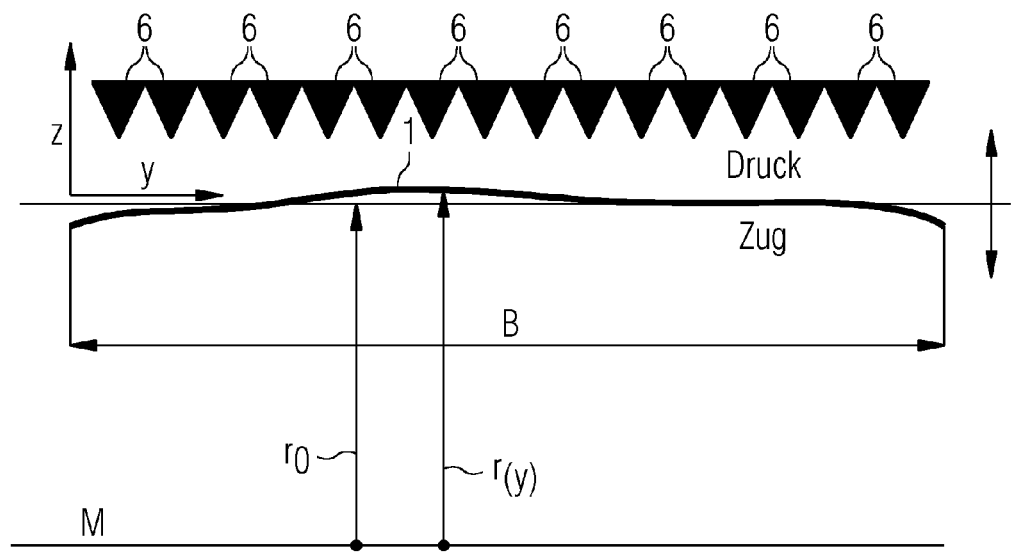
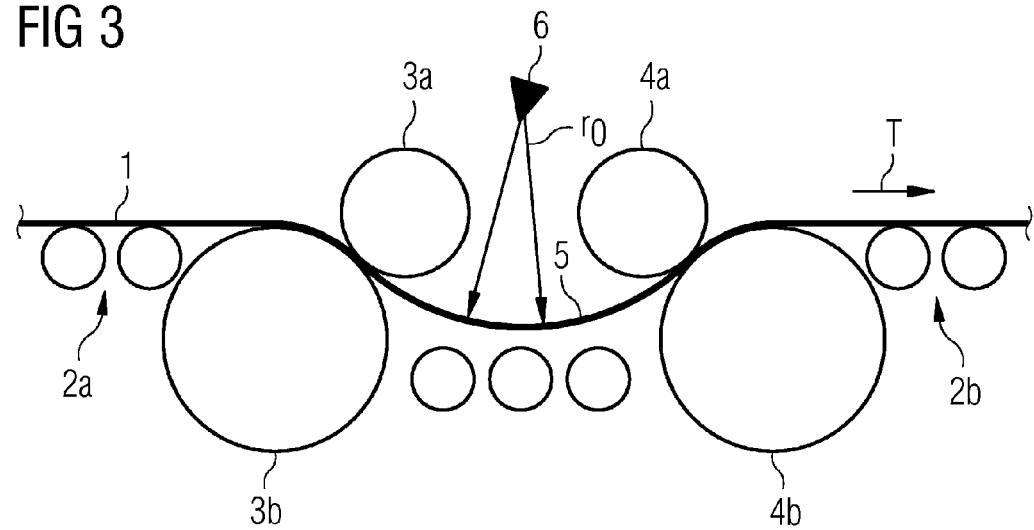

FLATNESS MEASURING AND MEASURING OF RESIDUAL STRESSES FOR A METALLIC FLAT PRODUCT

CROSS-REFERENCE TO RELATED APPLICATIONS

The present application is a 35 U.S.C. §§ 371 national phase conversion of PCT/EP2013/074563, filed Nov. 25, 2013, which claims priority of German Patent Application No. A50572/2012, filed Dec. 11, 2012, the contents of which are incorporated by reference herein. The PCT International Application was published in the German language.

FIELD OF TECHNOLOGY

The present invention relates to a method for measuring the flatness of a metallic flat product, a method for measuring the residual stresses in a metallic flat product and an apparatus for measuring flatness or for measuring the residual stresses in a metallic flat product.

When producing a metallic flat product, preferably made of steel or aluminum (for example steel strip), in a hot or cold rolling mill or when controlling the quality of the flat product or a sheet, it is advantageous if the flatness of the flat product can be determined with a high level of accuracy. In principle non-contact (also referred to as contactless) and contact (in other words non-contactless) measuring methods are known to the person skilled in the art. The non-contactless measuring methods (e.g. using pressure-sensitive measuring rollers) have the disadvantage that contact with the measuring roller cools the flat product and the measuring rollers can easily be contaminated by scale (particularly during hot rolling) or other dirt. Also non-contactless flatness measuring requires a defined minimum tension, with the result that on the one hand measuring accuracy is adversely affected and on the other hand for example the flatness of a tensionless strip head or strip foot cannot be determined. Contactless measuring methods have the disadvantage that they are insufficiently accurate.

PRIOR ART

Known from the dissertation

Fabian Loges: Development of new strategies for measuring and regulating strip flatness during flat rolling [in German], Kassel University Press, ISBN 978-3-89958-754-8, 2009 are various measuring methods and measuring devices for measuring flatness. The document does not demonstrate how the accuracy of methods for measuring flatness can be further improved.

SUMMARY OF THE INVENTION

One object of the invention is to improve further the accuracy and reliability of existing flatness measuring devices or methods for measuring flatness.

A further object of the invention is to specify a method and an apparatus for measuring the residual stresses in a metallic flat product.

The first-mentioned object is achieved by a method for measuring the flatness of a metallic flat product, preferably of a rolled product made of steel or aluminum, in particular of steel strip, having the following method steps:

bending the flat product in a bending device, so that after bending a planar flat product would form an arc with a target bending radius $r_0$;

measuring the contour, in particular the actual bending radii $r(y)$, in the region of the arc of the bent flat product in a number of positions (y), i.e. locations in the width direction of the flat product; and determining the flatness of the flat product taking into account the measured contour of the bent flat product.

Typically a metallic flat product (for example steel strip from a pre-rolling or finishing rolling line) is conveyed on a rolling conveyor in a horizontal plane. When the flatness is being measured, the flat product is bent to form an arc in a bending device, so that, assuming that the flat product is perfectly planar, the flat product forms a free arc with a target bending radius $r_0$.

When the flat product is being bent, it is advantageous if the flat product is bent upward to form an arc. The expression "upward to form an arc" refers to the bending up of the flat product, the center point of the arc of the bent flat product being located in a vertical direction below the apex of the arc. The fact that the flat product is bent "upward" means that dirt particles (e.g. scale) and also cooling water are removed automatically from the upper region of the arc (in particular from the apex), thereby improving the accuracy of the flatness measurement. Alternatively the flat product can of course also be bent "downward" or in a sideways direction in a horizontal plane.

The contour of the flat product is then measured, in particular by measuring the actual bending radii $r(y)$, in the region of the arc of the bent flat product in a number of positions (y) in the width direction of the flat product (in other words at right angles to the transport direction and at right angles to the thickness direction of the flat product). It is essentially irrelevant here whether flatness is measured in a contactless or non-contactless manner.

With the inventive method flatness is measured on the now bent previously flat product. Shape or flatness deviations therefore result in a change in the contour of the bent flat product. The contour is measured and the flatness determined therefrom.

In order to improve the accuracy of the flatness measurement, it is favorable if the flat product can form a "free arc" (in other words a non-clamped arc) at least in the measuring position (ideally also a longitudinal segment before and after the measuring position). Generally it is favorable if the measuring position is at the greatest possible distance in the transport direction from a bending device on the input side or on the output side.

After the contour of the bent flat product has been measured, the flatness of the flat product is determined taking into account the measured contour or the measured actual bending radii $r(y)$. The determination of flatness and common parameters therefor (e.g. I unit (I), height (H), % steepness (S), % elongation (e), and % flatness (f)) are known to the person skilled in the art for example from chapter 1 "Definitions of Geometrical Parameters" from V. B. Ginzburg. *High-quality steel rolling: theory and practice*, Marcel Dekker Inc., 1993.

After the contour has been measured the bent flat product is typically bent back again and the bent back flat product is conveyed on a rolling conveyor to the next processing step.

Normally flatness is measured between pre-rolling and finishing rolling or between finishing rolling and cooling of the flat product in a cooling section. It would be equally possible however for flatness to be measured after cooling and for example immediately before the strip is coiled. This allows the flatness of the strip to be determined in the ready for sale state.

In order to be able to assess the flatness of the flat product not only at right angles to the transport direction but also in the longitudinal direction, it is advantageous for the contour, in particular the actual bending radii r(x,y), of the bent flat product to be measured in a number of positions (x) or locations in the longitudinal direction of the flat product and for the flatness of the flat product to be determined for a number of positions (x) in the longitudinal direction of the flat product taking into account the measured contours of the bent flat product.

To achieve the most planar shape possible when further processing the flat product, e.g. during laser cutting, it is advantageous if the flatness of the flat product is stored and taken into account during further processing. It is particularly advantageous if the flatness of the flat product in both the width direction and the longitudinal direction is stored. The simplest way of taking into account flatness during further processing is to cut out regions of the flat product that are not sufficiently planar.

The second-mentioned object is achieved by a method for measuring the residual stresses of a metallic flat product, preferably of a flat product made of steel or aluminum, in particular of a steel strip, having the following method steps:

bending the flat product in a bending device, so that after bending a residual stress-free flat product forms an arc with a target bending radius $r_0$;

measuring the contour, in particular the actual bending radii r(y), in the region of the arc of the bent flat product in a number of positions (y) or locations in the width direction of the flat product;

calculating the residual stress $\sigma_x(y)$ of the flat product taking into account the measured contour of the bent flat product, for example by $$\sigma_x(y) = E \cdot \varepsilon_x(y) = E \cdot \frac{r_0 - r(y)}{r_0}.$$

A metallic flat product is also typically conveyed in a horizontal plane on a rolling conveyor before the residual stresses are measured. As when measuring flatness, the flat product is bent to form an arc in a bending device, so that the bent flat product forms a target bending radius $r_0$, assuming that the flat product is completely free of residual stresses.

The details given for measuring flatness remain the same for the two steps of bending the flat product and measuring the contour. Unlike when measuring flatness, the residual stress $\sigma_x(y)$ of the flat product is calculated from the measured contour, in particular the actual bending radii r(y), over the width of the flat product. The specified formula is sufficiently accurate for a one-dimensional stress state (as frequently occurs in rolled strips). Of course the corresponding relationships are also known to the person skilled in the art from mechanical science for more complicated stress states, such as a two-dimensional stress state for example.

With the inventive method the residual stresses are measured on the bent flat product, with the result that the residual stresses present locally in the flat product are permitted a spread (see FIG. 2b, in which regions with tensile stresses spread inward and regions with compressive stresses spread outward). The spread requires a change in the contour of the bent flat product. The contour is measured and the residual stresses are calculated therefrom.

In order to be able to assess the residual stresses of the flat product not only in one longitudinal position of the flat product, but also in a number of positions in the longitudinal direction, it is advantageous for the contour, in particular the actual bending radii r(x,y), of the bent flat product to be measured in a number of positions (x) in the longitudinal direction of the flat product and for the residual stress of the flat product to be calculated for a number of positions (x) on the flat product taking into account the measured contours of the bent flat product, for example by $$\sigma_x(x, y) = E \cdot \varepsilon_x(x, y) = E \cdot \frac{r_0 - r(x, y)}{r_0}.$$

It is particularly advantageous if the residual stresses $\sigma_x$ of the flat product are stored and taken into account during further processing. It is particularly advantageous if the residual stresses of the flat product in both the width direction and the longitudinal direction are stored. The simplest way of taking into account the residual stresses during further processing is to cut out regions with high or non-homogeneous residual stresses. This allows components to be produced with particularly accurate shapes. It is particularly advantageous to carry out a preliminary calculation of the shape (contour) of a component taking into account the (sometimes locally non-homogeneous) residual stresses, so that the component cut from a sheet subject to residual stresses has the desired shape after cutting out (see also FIGS. 9a, 9b).

The accuracy of the flatness measurement or the measurement of residual stress can be further improved, if the flat product is essentially tension-free and pressure-free, in other words subject to no or only minor tensile or compressive stresses during measuring. A sufficiently large number of options are known to the person skilled in the art in order to achieve this. For example the entry-side and/or exit-side torque of the entry rollers of the input-side bending device and/or of the exit rollers of the exit-side bending device can be set so that the flat product is approximately tension-free and pressure-free during measuring. Should said roller pairs be designed not to be driven, the torques could also be set by external drivers (i.e. drivers before the entry rollers or after the exit rollers in the transport direction) so that the flat product is kept approximately tension-free and pressure-free during measuring. A tension-free flat product (in particular strip) shows no deformations due to tension or pressure (e.g. constrictions), thereby improving the accuracy of the measurement.

Cooling of the flat product due to heat transfer when flatness is being measured or residual stress is being measured can be prevented if measuring is performed optically by means of a number of light beams, in particular laser beams, with a light beam being emitted from a light source onto the flat product, the light beam being reflected by the surface of the flat product and the reflected light beam being received by a receiver. The bending radius of the flat product as an indicator of flatness or residual stress can be determined over the overall distance between the emitter, the flat product and the receiver by means of the transit time of the light beam, by means of the phase difference between the emitted light beam and the received light beam or by means of triangulation. In the present application reflected also refers to diffuse reflection (scatter) at a surface.

A compact distance measuring device can be achieved if a light beam is emitted and received back by an emitter/receiver, in other words by a device that comprises both an emitter and a receiver.

In order to obtain a number of values for the contour of the flat product in its longitudinal and width directions, a number of light beams can be projected onto the flat product in the form of a light grid. The light beams are reflected by the surface of the flat product and the reflected light beams are received for example by one or more cameras. The camera images are preferably analyzed in real time.

A particularly simple emitter/receiver is moved in the width direction of the flat product (also referred to as traversing).

Alternatively a number of light sources and a number of receivers can be arranged in the width direction of the flat product, with measuring of the actual bending radii $r(y)$ taking place essentially simultaneously in the width direction of the bent flat product. This allows the flatness or residual stress of a moving flat product to be determined simultaneously in a number of positions—at right angles to the transport direction. It is advantageous here if the distance measurements in the number of positions are initiated simultaneously and analyzed within a sampling step of a measuring or regulating system.

The inventive method is particularly suitable for regulating the flatness of a metallic flat product, preferably of a flat product made of steel or aluminum, in particular of steel strip, in a rolling mill, having the following method steps:
  rolling a flat product in the rolling mill;
  measuring the flatness of the actual flatness $P_{Act}$ of the rolled flat product as disclosed herein;
  determining a regulating error e between a target flatness $P_{Tar}$ and the actual flatness $P_{Act}$, $e=T_{Tar}-P_{Act}$;
  determining a correcting variable u as a function of the regulating error e by means of a regulator;
  applying the correcting variable u to an actuator in a rolling stand of the rolling mill, so that the regulating error is minimized.

This keeps the flatness of the flat product at a high level even in different operating conditions. The actual flatness of a flat product (hot or cold) rolled in a rolling stand of a rolling mill and the deviation (the so-called regulating error) e between the target flatness $P_{Tar}$ and the actual flatness $P_{Act}$ are determined here. A regulator then uses the regulating error to determine a correcting variable u, which is supplied to at least one actuator (e.g. an actuator for roll deflection in a UC or CVC rolling stand) of the rolling stand, thereby minimizing the regulating error e. Such a measure allows flatness errors to be prevented during the rolling of the flat product. This allows undulations in the flat product (e.g. so-called long center, long edges, quarter buckles, edge buckles, center buckles, side buckles) etc. to be avoided; see also FIG. 1.13 "Forms of strip manifest shape" in the book by Ginzburg cited above).

It is particularly advantageous if the abovementioned method for regulating flatness is performed in a number of positions in the width direction of the flat product and the geometry of the flat product is influenced specifically by a number of actuators.

Accuracy can be further improved when measuring flatness or residual stress if during, shortly before, preferably immediately before, or shortly after, preferably immediately after, the measuring of the contour or bending radii $r(y)$ of the bent flat product the temperature $T(y)$ of a (longitudinal) fiber of the flat product is measured in the width direction (y) and the temperature $T(y)$ of the fiber is taken into account when determining flatness or calculating the residual stress.

This takes into account the influence of local thermal expansion of the flat product on r, so that it is possible as a result for example also to determine the flatness or residual stresses of the edge of the strip, which is often colder during hot rolling, with a high level of accuracy. Measuring can be performed for example using pyrometers or an infrared camera. As an alternative to measuring, the temperature distribution in the flat product, e.g. during hot rolling, could be determined using a calculation model. This is preferably done online. The local temperatures in the strip can also be determined using a combination of an upstream and/or downstream measurement and a calculation model. The calculation model takes into account for example the thermal capacity and thermal conductivity of the strip, the emissivity, convection, ambient temperatures and thermal radiation of the environment.

The object cited in the introduction is also achieved by an apparatus for measuring flatness or for measuring the residual stresses of a metallic flat product, having:
  an input-side rolling conveyor for conveying the flat product;
  an input-side bending device having at least two entry rollers for bending the flat product, so that the bent flat product can form a bending radius $r_0$;
  a distance measuring device for measuring the contour, in particular the actual bending radii $r(y)$, of the bent flat product in a number of positions in the width direction of the flat product;
  a computation unit for determining the flatness or residual stresses of the flat product, which is connected to the distance measuring device for the purpose of exchanging signals.

The input-side rolling conveyor conveys the flat product to the apparatus for measuring flatness or for measuring the residual stresses of the metallic flat product. The two entry rollers of the input-side bending device, which typically lie opposite one another in the thickness direction of the flat product, bend the flat product in such a manner that the bent flat product forms a bending radius $r_0$—assuming that the flat product is essentially planar when measuring flatness or essentially free of residual stresses. The distance measuring device can be used to measure the contour of the flat product in a number of positions in the width direction of the flat product. The computation unit—which is connected to the distance measuring device for the purpose of exchanging signals—can determine the flatness or the residual stresses of the flat product from the contour of the bent flat product.

It is expedient if the distance measuring device is an optical flatness measuring device. Alternatively the distance measuring device can have a number of contact rollers offset in the width direction of the flat product.

In order to prevent the penetration of dirt into the distance measuring device, it is advantageous if the distance measuring device is arranged in a vertical direction above the flat product. It is also advantageous if the distance measuring device is arranged in a horizontal direction in the region of the apex of the arc of the bent flat product.

It is expedient if the apparatus also comprises an output-side bending device having at least two exit rollers for bending back the flat product; and an output-side rolling conveyor for conveying the flat product.

The tension of the flat product can be set by the inventive apparatus, in that at least one roller of the entry rollers is configured so that it can be driven to bend the flat product and/or at least one roller of the exit rollers is configured so that it can be driven to bend back the flat product.

Relatively small bending radii $r_0$ are advantageously used when detecting relatively high-frequency undulations in the flat product. Relatively large bending radii $r_0$ are adequate for the detection of relatively low-frequency undulations. If both high and low-frequency undulations are to be resolved with a high level of accuracy, an apparatus can have variable bending radii $r_0$ (see FIG. 7).

BRIEF DESCRIPTION OF THE DRAWINGS

Further advantages and features of the present invention will emerge from the description which follows of non-restrictive exemplary embodiments, with reference being made to the figures below, in which:

FIG. 2b: shows a side view of the strip from FIG. 1.

FIG. 3: shows a schematic representation of an alternative apparatus to the one in FIG. 1.

DESCRIPTION OF EMBODIMENTS

Figure 1:
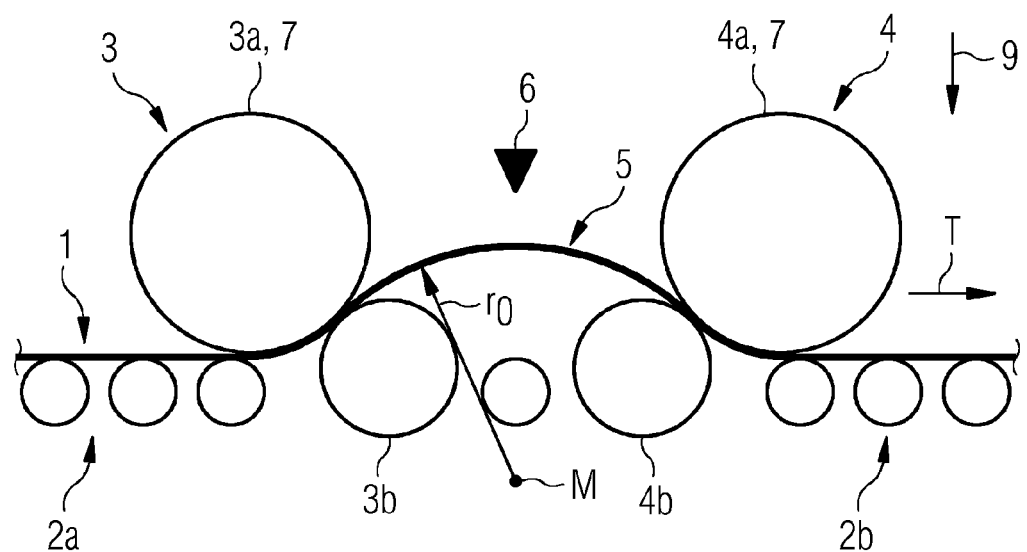
FIG. 1: shows a schematic representation of an inventive apparatus for measuring flatness or for measuring the residual stresses of a flat product.

FIG. 1 shows a schematic representation of an apparatus for measuring flatness or for measuring the residual stresses in a flat product 1 configured as steel strip. After the strip has been rolled in a rolling stand of a finishing rolling line (not shown), the strip 1 is conveyed by an input-side rolling conveyor 2a in a horizontal direction to the input-side bending device 3 with a pair 3a, 3b of entry rollers embodied as driver rollers 7 engaging the strip at its opposite surfaces. The entry rollers 3a, 3b are located relative to the horizontal direction above the path of the strip 1 to bend the strip 1 upward, forming an arc 5 in the strip with a radius of curvature $r_0$ about the center point M of the arc assuming that the strip is planar or free of residual stresses. The arc 5 is free between the contact lines of the entry rollers 3a, 3b and the contact lines of the exit rollers 4a and 4b, in other words it is not conveyed in this arc region. Arranged above and roughly in the region of the apex of the arc 5 are a plurality of distance measuring devices 6. In the example shown, each light source of a distance measuring device 6 emits a laser beam, which is reflected by the surface of the arc 5 and received back by the receiver in the distance measuring device 6. Thus the distance measuring devices 6 determine the contour of the strip in a number of positions y in the width direction of the strip 1. More specifically, the contour of the strip 1 is determined for example based on the transit time of the laser beam or the phase shift of the reflected light beam in relation to the emitted light beam, allowing the slightest deviations in the contour of the strip to be determined.

Figure 2A:
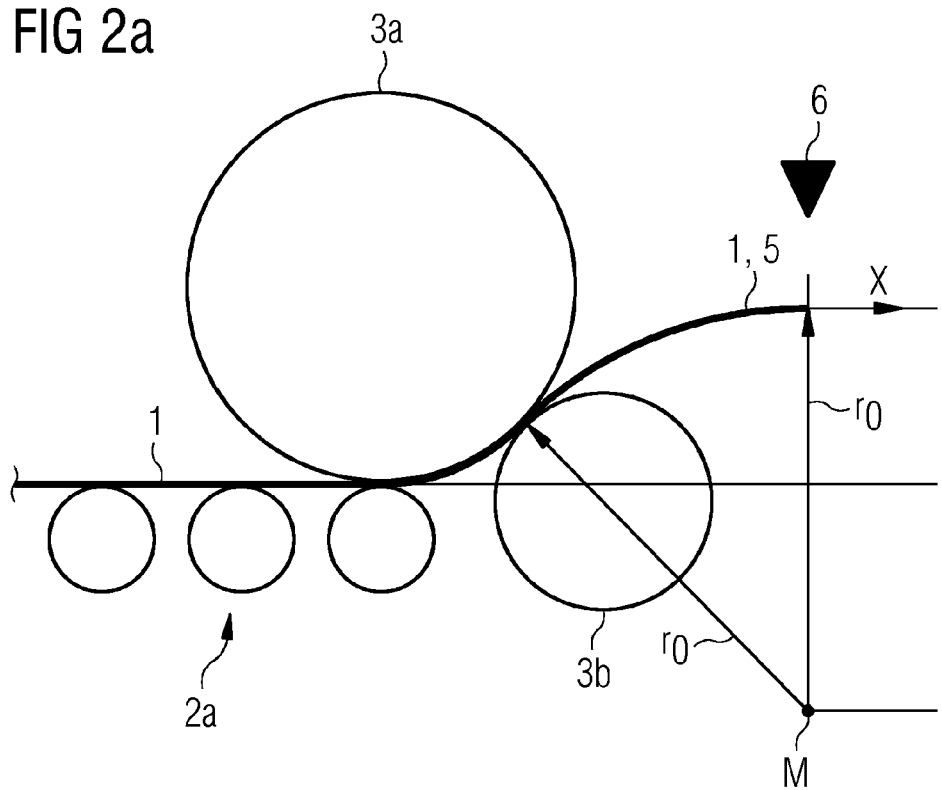
FIG. 2a: shows a detail of FIG. 1.

As shown in FIG. 2a a number of, in this instance 16, distance measuring devices 6 may be arranged in the width direction y of the strip 1. Alternatively, one distance measuring device 6 may traverse in the width direction y of the flat product.

After the contour has been measured, the strip 1 is bent again by the two exit rollers 4a, 4b above the path set by output side conveyor 2b in the transport direction T and then conveyed on the output-side rolling conveyor 2b in a horizontal transport direction T to a cooling section (not shown). In order for the flatness or residual stress measurement not to be falsified by tension or pressure in the strip, the strip is roughly tension-free and pressure-free in the region of the arc 5. This is achieved for example in that both the entry rollers 3a, 3b and the exit rollers 4a, 4b are embodied as driver rollers 7 and the drive torque of the driver rollers 7 is set so that the strip 5 is essentially tension/pressure-free during measuring.

The contour, in particular the actual bending radii r(y), of the strip is transmitted to a computation unit (not shown), which determines the flatness and/or the residual stresses of the strip and outputs it/them by way of an output unit. The distance measuring devices 6 are connected to the computation unit by way of a bus interface here.

In order not to be restricted to determining the flatness or the residual stresses of the strip 1 only in the width direction y, the strip 1 is moved in the transport direction T, while the distance measuring devices 6 determine the contour of the flat product. From the contour information, which is available for example in the form of a matrix (e.g. the 16 simultaneously analyzed actual bending radii r(y) of the flat product in the width direction can represent one row of the matrix; successive contour sampling steps are performed in adjacent rows of the matrix), it is possible to determine the flatness of the strip. With regard to the formulas for common flatness parameters reference is made to chapter "1.18 *Formulas for Strip Flatness*" in V. B. Ginzburg. High-quality steel rolling: theory and practice, Marcel Dekker Inc., 1993.

To distinguish between up and down, gravity g is shown in FIG. 1.

FIG. 2a shows a detail from FIG. 1.

FIG. 2b shows a side view of the bent up strip 1 with 16 distance measuring devices 6 distributed over the width B of the strip 1. Each distance measuring device 6 emits a laser beam onto the strip 1, which is reflected by the strip 1 and received back by the distance measuring device 6. The analysis of the laser beam allows the actual bending radii r(y) to be determined over the width direction y of the strip 1. The analysis of the contour in the width direction y also allows other shape deviations to be determined, for example a so-called camber of a strip clamped on the entry and exit sides. This is expressed in a gradient of the contour in the y-z plane.

Like the flatness, the residual stresses in the flat product 1 are determined based on the contour of the flat product 1. The residual stress $\sigma_x(y)$ of the flat product 1 in the x direction is as follows in a position y in the width direction:

$$\sigma_x(y) = E \cdot \varepsilon_x(y) = E \cdot \frac{r_0 - r(y)}{r_0},$$

where E is the modulus of elasticity of the flat product, $\epsilon_x(y)$ is the elongation in the x direction in position y, r(y) is the measured actual bending radius in position y, and $r_0$ is the nominal bending radius of the flat product in the apparatus. In a simplified calculation $r_0$ can be assumed to be the mean radius r(y) over the width B.

FIG. 3 shows an alternative to the apparatus shown in FIG. 1, in which the strip 1 is bent down. In order to avoid measuring being influenced by scale or cooling water, the arc 5 is blown free using compressed air.

Figure 4:
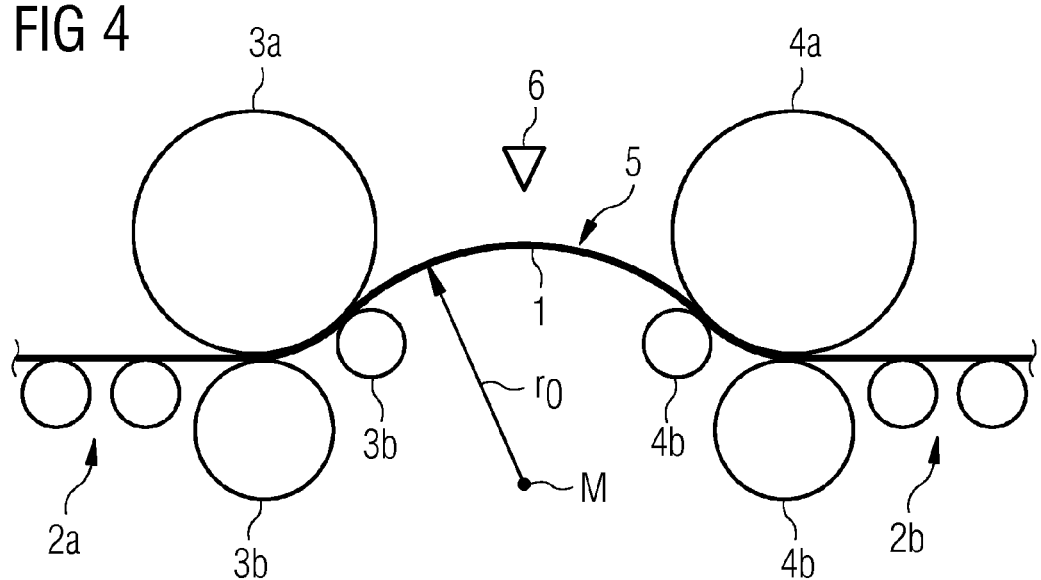
FIGS. 4 and 5: show respective schematic representations of a first and a second variant of the apparatus shown in FIG. 1.
Figure 5:
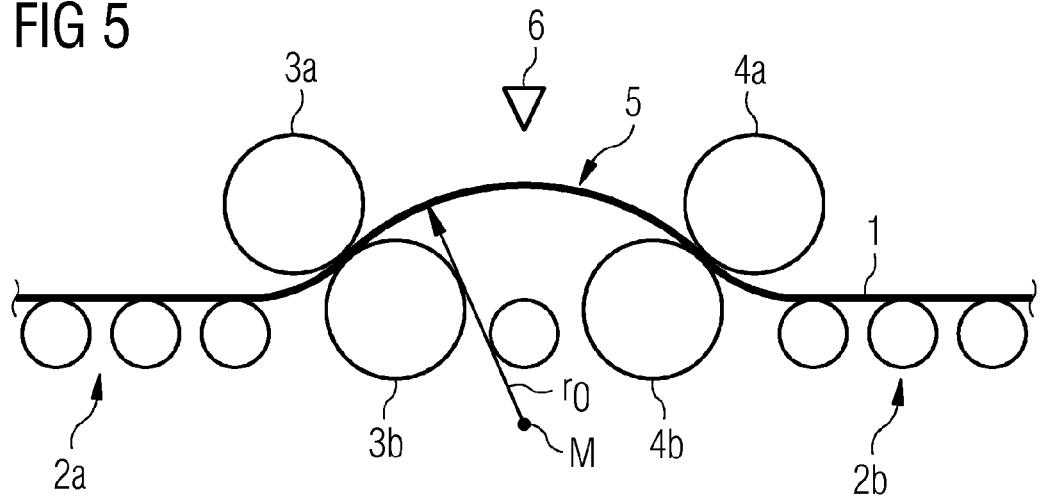

FIGS. 4 and 5 show two further inventive alternatives to FIG. 1. In FIG. 4 the entry rollers comprise an upper roller 3a and two lower rollers 3b. The same applies to the exit rollers 4a, 4b. In FIG. 5 the upper and lower entry rollers 3a, 3b respectively and the exit rollers 4a, 4b have the same diameter.

Figure 6A:
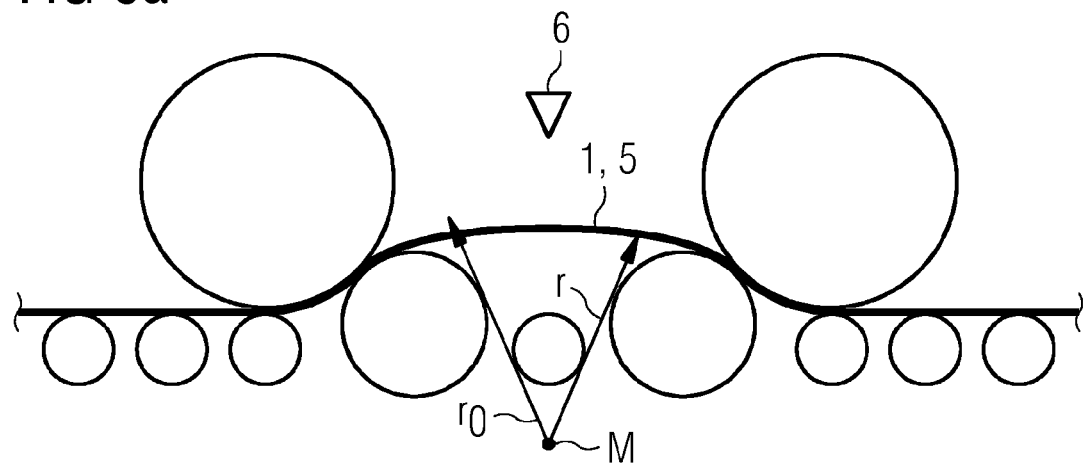
FIGS. 6a and 6b: show respective representations of the arc from FIG. 1 with different strip tensions.
Figure 6B:
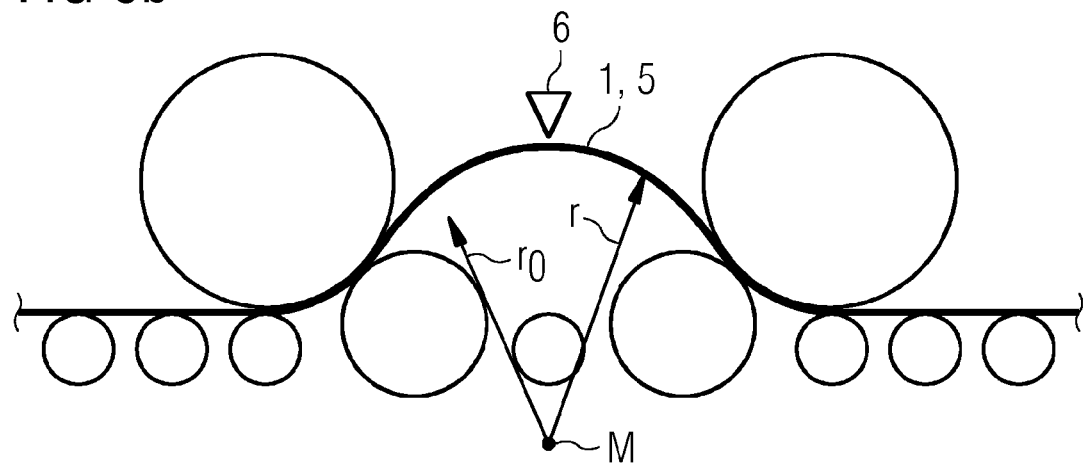

FIGS. 6a and 6b show the apparatus shown in FIG. 1, with an increased strip tension in the strip 1 in FIG. 6a compared with FIG. 1 and a reduced strip tension in FIG. 6b compared with FIG. 1. The actual bending radius in FIGS. 6a, 6b is shown as r; the nominal bending radius from FIG. 1 is $r_0$. Analysis of the actual bending radius r also allows the tension of the strip 1 to be set specifically. The arc 5 between the entry rollers 3a, 3b and the exit rollers 4a, 4b also serves as a buffer, so that short-term fluctuations between the entry and exit only result in minor tension fluctuations.

Figure 7:
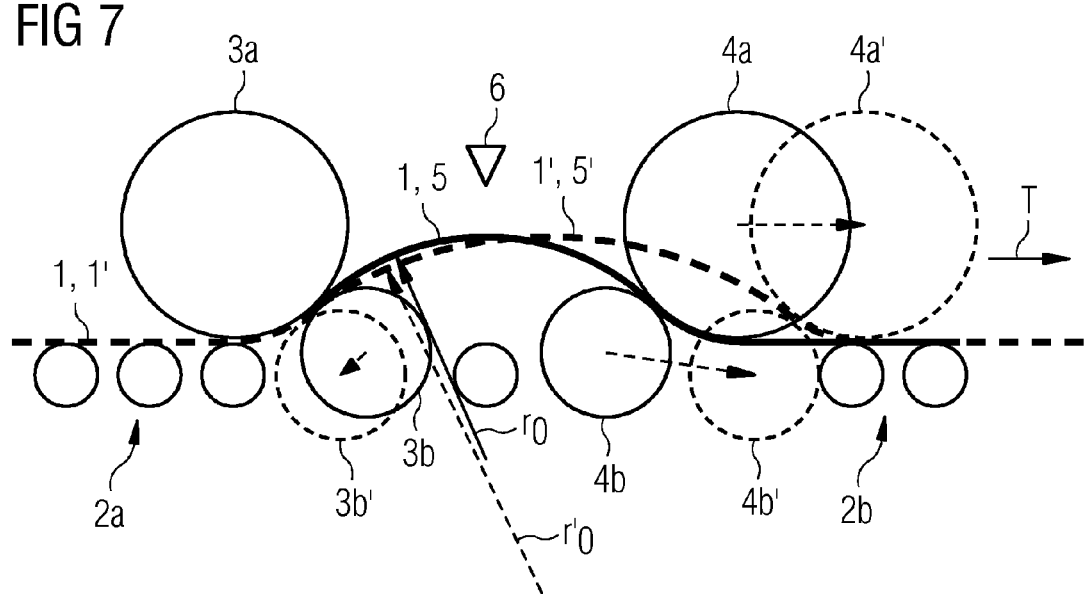
FIG. 7: shows a representation of the apparatus shown in FIG. 1 with modifiable $r_0$ and modifiable arc length for thin and thick strip.

In principle the inventive method and the inventive apparatus are suitable for both thin and relatively thick flat products. FIG. 7 shows the changes required in the apparatus going from a thin strip 1 to a relatively thick strip 1'. More specifically the lower entry roller 3b is moved to some degree counter to the transport direction T and to some degree in a downward direction, the upper and lower exit rollers 4a, 4b are each moved—as shown by dashed arrows—in the transport direction T and the roller 4b is moved to some degree in a downward direction symmetrically to 3b. This increases the radius of curvature $r_0'$ of the arc 5' for the thick strip 1' compared with the radius of curvature $r_0$ of the arc 5 for the thin strip 1.

Figure 8:
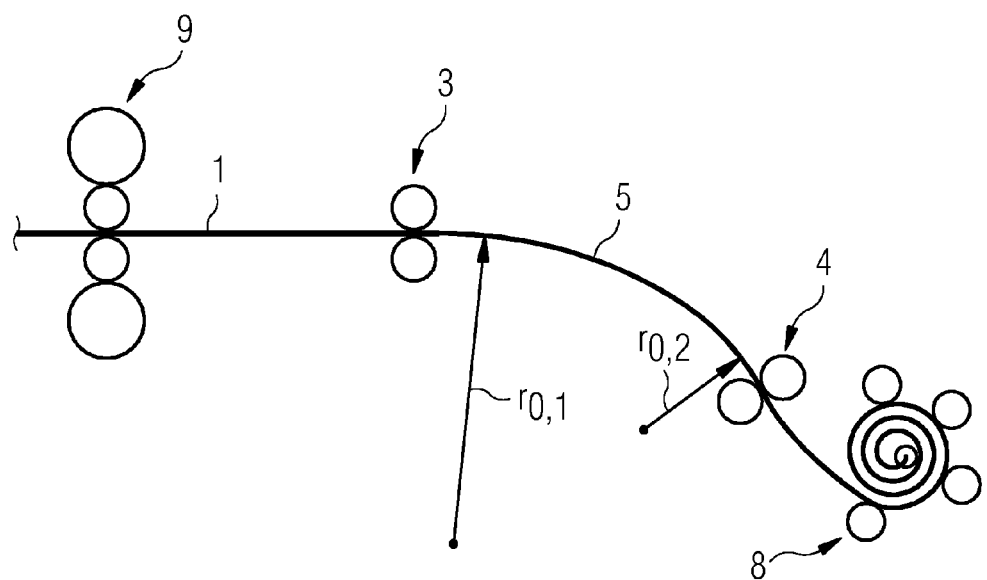
FIG. 8: shows a representation of an inventive apparatus having a variable bending radius $r_0$ over the longitudinal extension.

FIG. 8 shows a modified apparatus for measuring flatness or for measuring the residual stresses in the flat product 1, wherein the bending radii r is not constant over the longitudinal extension of the flat product 1. More specifically the bending radius after the input-side bending device 3 is $r_{0,1}$ and shortly before the output-side bending device 4 $r_{0,2}$, where $r_{0,1} > r_{0,2}$. The flat product 1 is coiled after measuring by contour measuring devices 6 (not shown) onto a reel 8. In order to improve the accuracy of the flatness measurement or the residual stress measurement further, the contour of the flat product 1 can be acquired in a number of positions in the longitudinal direction of the flat product 1 in the region of the arc 5. The flatness or residual stress is calculated in each instance from the contours. The at least partially redundant contour information can be used to improve the accuracy of the measurements; for example the results of measuring the flatness or residual stress can be averaged.

Figure 9A:
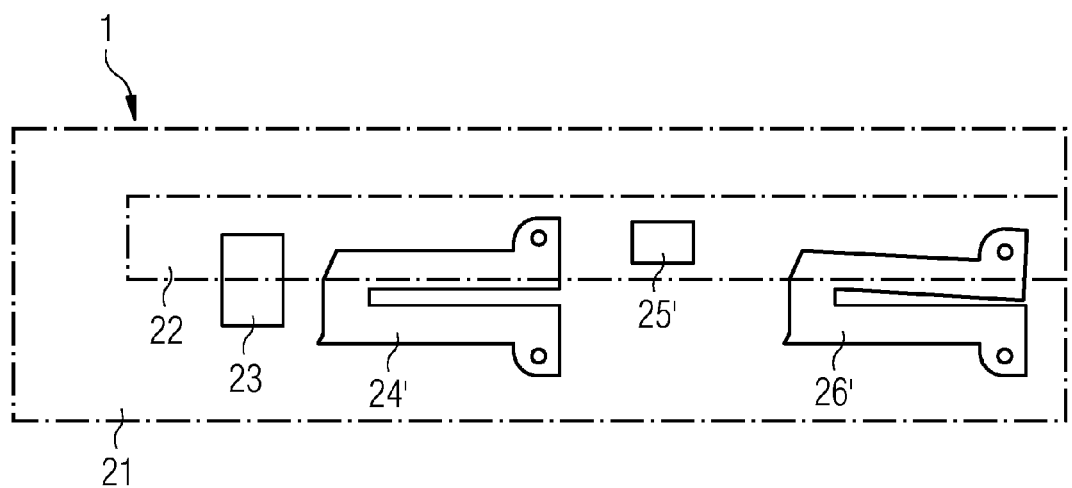
FIGS. 9a and 9b: show a representation of the influence of tensile stresses in the flat product on a subsequent production process.
Figure 9B:
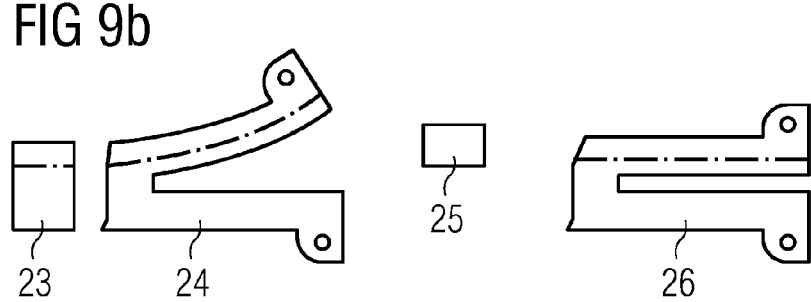

FIGS. 9a and 9b show that the knowledge of the residual stresses in a flat product is also important for further production steps. FIG. 9a shows a steel strip 1, which has a region 22 with tensile stresses and away from 22 a region 21 without tensile stresses. The sectional shapes 23'-26' of different components 23-26 are also shown, said components being cut out from the flat product 1 using a laser cutting machine. The influence of the tensile stresses on the resulting shapes of the components 23-26 is shown in FIG. 9b. As shown in FIG. 9b, the upper part of the component 24 bends up due to the tensile stresses 22, having an adverse effect on dimensional stability. The same is true of the upper part of the component 23. In any case it can been seen from the representations that the knowledge of the residual stresses is extremely important when manufacturing high-precision components, as otherwise significant component distortion is possible. The sectional shape 26' was determined taking into account the determined residual stress distribution in the sheet-like flat product 1, so that the shape of the component 26 corresponds as far as possible to the desired shape after cutting out.

Although the invention has been illustrated and described in detail using the preferred exemplary embodiments, the invention is not restricted by the disclosed examples and other variations can be derived therefrom by the person skilled in the art without departing from the scope of protection of the invention.

LIST OF REFERENCE CHARACTERS

1 Flat product
2a Input-side rolling conveyor
2b Output-side rolling conveyor
3 Input-side bending device
3a Upper entry roller
3b Lower entry roller
4 Output-side bending device
4a Upper exit roller
4b Lower exit roller
5 Arc
6 Distance measuring device
7 Drive roller
8 Reel
9 Rolling stand
21 Region without tensile stresses
22 Region with tensile stresses
23' . . . 26' Sectional shape of components
23 . . . 26 Components
B Width of the flat product
Gravity
M Center point
r, $r_0$ Radius of curvature
T Transport direction of the flat product
x, y, z x,y,z axis of a Cartesian coordinates system

The invention claimed is:
1. A method for measuring the flatness of a metallic flat product, comprising the following method steps:
    bending the flat product at a location along the longitudinal direction of the flat product, so that after the bending, the planar flat product forms an arc along the location having a target bending radius $r_0$;
    measuring a contour of the flat product in a region along the arc by measuring the actual bending radii r(y), in the region along the arc, of the bent flat product at a plurality of positions (y) in a width direction across the flat product; and
    determining the flatness of the flat product by taking into account the measured contour of the bent flat product along the length of the arc and across the width of the flat product at the arc.
2. The method as claimed in claim 1, further comprising measuring the contour of the flat product by measuring the actual bending radii r(x,y) of the bent flat product at a plurality of positions (x) along the longitudinal direction of the flat product; and determining the flatness of the flat product at a number of locations (x) along the longitudinal direction of the flat product taking into account the measured contours of the bent flat product.

3. The method as claimed in, claim 1, further comprising storing the determined flatness of the flat product and taking the stored flatness into account during further processing of the flat product.

4. A method for measuring the residual stresses of a metallic flat product comprising the following method steps:
bending the flat product, so that after the bending, a residual stress-free flat product forms an arc along the location having a target bending radius $r_0$;
measuring a contour of the flat product at the arc by measuring actual bending radii r(y), in a region along the arc, of the bent flat product in a plurality of positions(y) in a width direction across the flat product;
calculating the residual stress $\sigma_x(y)$ of the flat product taking into account the measured contour of the bent flat product.

5. The method as claimed in claim 4, further comprising:
measuring the contour of the flat product at the arc by measuring the actual bending radii r(x,y), of the bent flat product in a plurality of positions (x) along the longitudinal direction of the flat product; and
calculating the residual stress $\sigma_x(x,y)$ of the flat product for a number of positions in the longitudinal direction (x) of the flat product taking into account the measured contours of the bent flat product.

6. The method as claimed in claim 5, further comprising storing the residual stresses $\sigma_x$ of the flat product and then taking the residual stresses into account during further processing of the flat product.

7. The method as claimed in claim 1, further comprising:
measuring an actual bending radius r optically by at least one light beam, emitting the light beam from a light source onto a surface of the flat product along the arc;
reflecting the light beam from the surface of the flat product receiving the reflected light beam by a receiver; and
determining the distance between the light source, and the flat product and between the flat product and the receiver by the transit time of the light beam, by the phase difference between the emitted light beam and the received light beam or by means of triangulation.

8. The method as claimed in claim 7, further comprising:
projecting a number of light beams onto a surface of the flat product along the arc for defining a light grid; and
reflecting the light beams from the surface of the flat product and receiving the reflected light beams by a camera.

9. The method as claimed in claim 7, further comprising arranging a number of light sources and a number of receivers along the width direction (y) of the flat product along the arc and measuring the actual bending radii r(y) essentially simultaneously in the width direction (y) of the bent flat product.

10. A method for regulating the flatness of a metallic flat product, in a rolling mill, comprising the following method steps,
rolling the flat product in the rolling mill;
measuring the actual flatness $P_{Act}$ of the rolled flat product claimed in claim 1;
determining a regulating error e between a target flatness $P_{Tar}$ and the actual flatness $P_{Act}$, $e=P_{Tar}-P_{Act}$;
determining a correcting variable u as a function of the deviation e by means of a regulator;
applying the correcting variable u to an actuator in a rolling stand of the rolling mill, so that the regulating error e is minimized.

11. The method as claimed in claim 1, further comprising at least one of during, shortly before, immediately before, shortly after, and immediately after measuring the contour of the bent flat product, measuring the temperature T(y) of a fiber of the flat product in the width direction (y) and taking the temperature T(y) into account when determining flatness or calculating the residual stress.

12. An apparatus for measuring flatness or for measuring the residual stresses of a metallic flat product, the apparatus comprising:
an input-side rolling conveyor located and configured for conveying the flat product;
an input-side bending device following the input side rolling conveyor and comprised of at least two entry rollers for contacting opposite surfaces of the flat product, the entry rollers being located for bending the flat product, to form a bending radius $r_0$ in the flat product along a longitudinal length location of the flat product;
a distance measuring device for measuring the contour at the actual bending radii r(y), of the bent flat product at a plurality of positions in a width direction (y) of the flat product; and
a computation unit for determining the flatness or the residual stresses of the flat product and the computation unit is connected to the distance measuring device for the purpose of exchanging signals.

13. The apparatus as claimed in claim 12, wherein the distance measuring device comprises an optical, distance measuring device.

14. The apparatus as claimed in claim 12, further comprising the distance measuring device is arranged in a vertical direction above the flat product and in a horizontal direction in the region of an apex of the arc of the bent flat product.

15. The apparatus as claimed in claim 12, further comprising:
an output-side bending device comprised of at least two exit rollers at opposite surfaces of the flat product and located along the longitudinal length of the flat product spaced from the entry rollers and the exit rollers being configured for bending the bent flat product back toward an unbent condition; and
an output-side rolling conveyor located and configured for conveying the bent back flat product from the exit rollers.

16. The apparatus as claimed in claim 15, further comprising at least one of the entry rollers of the input-side bending device is drivable to bend the flat product and/or driving at least one exit roller of the output-side bending device to bend back the bent flat product.

17. The apparatus as claimed in claim 15, wherein at least one of the entry and the exit rollers are drivable so as to form an arc in the flat product along the longitudinal direction of the flat product between the entry and the exit rollers.

18. The method as claimed in claim 4, wherein the calculation of the residual stress of the flat product takes into account the measured contours of the bent flat product according to the formula $$\sigma_x(y) = E \cdot \varepsilon_x(y) = E \cdot \frac{r_0 - r(y)}{r_0}$$

wherein E is the modulus of elasticity of the flat product, $\epsilon_x(y)$ is the elongation in the x direction in position y, r(y) is the measured actual bending radius in position y, and $r_0$ is the nominal bending radius of the flat product in the apparatus or the mean radius r(y) over the width B.

19. The method according to claim 5, wherein the calculation of the residual stress of the flat product takes into account the measured contours of the bent flat product according to the formula $$\sigma_x(x, y) = E \cdot \varepsilon_x(x, y) = E \cdot \frac{r_0 - r(x, y)}{r_0}$$

wherein E is the modulus of elasticity of the flat product, $\epsilon_x(y)$ is the elongation in the x direction in position y, r(y) is the measured actual bending radius in position y, and $r_0$ is the nominal bending radius of the flat product in the apparatus or the mean radius r(y) over the width B.

20. The method according to claim 7, wherein the at least one light beam is a laser beam.

\* \* \* \* \*